(12) United States Patent
Bergström et al.

(10) Patent No.: US 11,826,236 B2
(45) Date of Patent: Nov. 28, 2023

(54) MEDICAL DRESSING

(71) Applicant: Mölnlycke Health Care AB, Gothenburg (SE)

(72) Inventors: Maria Gustin Bergström, Linköping (SE); Linda Östlund, Kungsbacka (SE); Lena Jacobsson, Gothenburg (SE); Christian Wathne, Mölnlycke (SE)

(73) Assignee: Mölnlycke Health Care AB, Gothenburg (SE)

(*) Notice: Subject to any disclaimer, the term of this patent is extended or adjusted under 35 U.S.C. 154(b) by 829 days.

(21) Appl. No.: 15/775,456

(22) PCT Filed: Nov. 8, 2016

(86) PCT No.: PCT/EP2016/076988
§ 371 (c)(1),
(2) Date: May 11, 2018

(87) PCT Pub. No.: WO2017/081012
PCT Pub. Date: May 18, 2017

(65) Prior Publication Data
US 2018/0353343 A1 Dec. 13, 2018

(30) Foreign Application Priority Data
Nov. 13, 2015 (EP) .................................... 15194495

(51) Int. Cl.
*A61F 13/02* (2006.01)

(52) U.S. Cl.
CPC ...... *A61F 13/0263* (2013.01); *A61F 13/0259* (2013.01); *A61F 13/0226* (2013.01); *A61F 13/0246* (2013.01)

(58) Field of Classification Search
CPC .. A61F 13/02; A61F 13/0203; A61F 13/0206; A61F 13/0209; A61F 13/0213;
(Continued)

(56) References Cited

U.S. PATENT DOCUMENTS

| | | |
|---|---|---|
| 4,485,809 A | 12/1984 | Dellas |
| 4,614,183 A * | 9/1986 | McCracken .......... A61F 13/023 |
| | | 602/57 |

(Continued)

FOREIGN PATENT DOCUMENTS

| | | | |
|---|---|---|---|
| CN | 1756570 | 4/2006 | |
| GB | 2527617 A * | 12/2015 | ....... A61F 13/00008 |

(Continued)

OTHER PUBLICATIONS

International Search Report and Written Opinion dated Jan. 3, 2017 by the International Searching Authority for Patent Application No. PCT/EP2016/076988, which was filed on Nov. 8, 2016 and published as WO 2017/081012 on May 18, 2017 (Inventor—Gustin Bergström et al.; Applicant—Mölnlycke Health Care AB) (8 pages).

(Continued)

*Primary Examiner* — Ophelia A Hawthorne
*Assistant Examiner* — Kevin S Albers
(74) *Attorney, Agent, or Firm* — Ballard Spahr LLP

(57) ABSTRACT

The present invention relates to a dressing having a lateral (x) and a longitudinal (y) extension. The dressing comprises a backing layer, a wound pad contoured by a pair of lateral edges extending in parallel to each other in the lateral direction, and an adhesive layer having a wound facing surface and a non-wound facing surface. The wound pad is arranged between the backing layer and the adhesive layer, and the backing layer extends beyond the periphery of the wound pad to define a border portion along the contour of the wound pad. A release liner is releasably attached to the (Continued)

wound facing surface of the adhesive layer. The release liner is divided by a first dividing line extending in the lateral direction of the dressing to form at least a first removable portion, and a second removable portion, wherein the first and the second portions overlap along the first dividing line to form a first grip member.

20 Claims, 5 Drawing Sheets

(58) Field of Classification Search
  CPC ............ A61F 13/0216; A61F 13/022; A61F 13/0223; A61F 13/0226; A61F 13/023; A61F 13/0233; A61F 13/0236; A61F 13/024; A61F 13/0243; A61F 13/0246; A61F 13/025; A61F 13/0253; A61F 13/0256; A61F 13/0259; A61F 13/0263; A61F 13/0266; A61F 13/0269; A61F 13/0273; A61F 13/0276; A61F 13/0279; A61F 13/0283; A61F 13/0286; A61F 13/0289; A61F 13/0293; A61F 13/0296; A61F 2013/008; A61F 2013/00817
  See application file for complete search history.

(56) References Cited

U.S. PATENT DOCUMENTS

| | | | | |
|---|---|---|---|---|
| 4,807,613 A | * | 2/1989 | Koehnke | A61F 13/0203 206/440 |
| 5,042,466 A | * | 8/1991 | McKnight | A61F 13/023 602/57 |
| 5,052,381 A | * | 10/1991 | Gilbert | A61F 13/023 602/57 |
| 6,566,575 B1 | * | 5/2003 | Stickels | A61F 13/023 602/41 |
| 10,016,544 B2 | * | 7/2018 | Coulthard | A61F 13/022 |
| 2006/0151347 A1 | | 7/2006 | Grossman | |
| 2008/0051688 A1 | * | 2/2008 | Lowe | A61F 13/023 602/58 |
| 2009/0105670 A1 | | 4/2009 | Bentley et al. | |
| 2010/0159191 A1 | | 6/2010 | Cotton | |
| 2010/0159192 A1 | * | 6/2010 | Cotton | A61L 15/58 428/137 |
| 2011/0282309 A1 | * | 11/2011 | Adie | A61F 13/0209 604/319 |
| 2012/0234484 A1 | * | 9/2012 | Takada | A61P 17/00 156/60 |
| 2012/0316519 A1 | * | 12/2012 | Uematsu | A61F 13/00063 156/306.6 |
| 2014/0121620 A1 | * | 5/2014 | Hung | A61F 13/0226 604/385.05 |
| 2016/0045376 A1 | * | 2/2016 | Nielsen | A61F 13/025 602/55 |
| 2016/0089145 A1 | * | 3/2016 | Quintero | A61F 13/0263 606/216 |

FOREIGN PATENT DOCUMENTS

| | | |
|---|---|---|
| JP | 3135535 | 8/2019 |
| KR | 200357036 | 7/2004 |
| WO | WO 2004/060412 | 7/2004 |
| WO | WO 2014075684 | 5/2014 |

OTHER PUBLICATIONS

European Opposition (27 pages) filed Oct. 2, 2020, in application No. EP 16791613.9.

* cited by examiner

MEDICAL DRESSING

CROSS-REFERENCE TO RELATED APPLICATIONS

This application is a U.S. National Phase Application of International Application No. PCT/EP2016/076988, filed Nov. 8, 2016, which claims priority to European Application No. 15194495.6, filed Nov. 13, 2015, each of which are hereby incorporated by reference in their entirety.

FIELD OF THE INVENTION

The present invention relates to a dressing comprising a backing layer, a wound pad and an adhesive layer. A release liner is releasably attached to the wound facing surface of the adhesive layer. The release liner comprises at least a first and a second removable portion, which overlap to form a first grip member.

BACKGROUND OF THE INVENTION

Wound dressings comprising a thin, self-adhesive wound covering membrane have gained wide acceptance in managing wounds due to their pliability and ability to conform well to the contours of the skin. Such dressings typically comprise a wound contact layer with an adhesive coating. The purpose of the adhesive is to adhere to the wound and/or to the skin surrounding the wound and to fixate the dressing in a desirable position. The adhesive used needs to be gentle to the skin.

While thinness and adhesiveness of the dressing is desirable, the dressings are typically difficult to handle and to apply to a patient. The dressings are not self-supporting, and may wrinkle or stick to themselves during application. The wrinkles formed may produce thin channels through which fluid is able to leak. Accordingly, the dressings become useless, and must ultimately be discarded.

In order to facilitate the handling of thin adhesive film dressings, a release liner may be attached to the adhesive coating. However, once the release liner has been removed, the adhesive coated film can still wrinkle and adhere to itself.

Thin film adhesive dressings are often applied following surgery, and should initially be sterile for medical applications. Surgical wounds face many challenges. Patients may develop blisters, which may increase patient discomfort and pain, delay surgical wound healing and increase the risk of surgical site infections. In surgical environments, sterility is key, and aseptic application of dressings is fundamental. Users, such as clinicians must apply the dressings under strict aseptic conditions. It is important not to touch the surface of the dressing in order to avoid contamination of the dressing layer.

Various attempts have been made to facilitate the handling and application of thin adhesive dressings. For example, US2009/0105670 discloses a composite structure comprising a cover, a stiffener and a releasable liner. The stiffener and the releasable liner, which comprises three laterally located sections, provide stiffness to the composite structure and prevents the dressing from sticking to itself and wrinkle upon application. The stiffener is releaseably secured to the upper surface of the cover and includes a handle being more rigid than the principal portion of the stiffener.

U.S. Pat. No. 4,614,183 discloses a polymeric film dressing whose adhesive surface is covered by a release paper liner formed in three laterally disposed sections. The central section is arranged to be removed first, and the dressing is grasped by the two side sections to place it in the desired position. Finally, the side sections are removed to complete the securement of the dressing to a wound.

While the above described documents offer solutions to the problem of handling thin film dressings by utilizing three piece release liner systems, there is still a risk that, upon application of the dressing, the side sections of the dressing covered by the release liner may fall down onto the wound, or that a user may interfere with the incision during the removal process of the side sections of the release liner. This may result in contamination of the wound site. Hence, there is a need to improve and simplify the application of thin film dressings such that the risk of touching or interfering with the incise is minimized.

SUMMARY OF THE INVENTION

It is an object of the present invention to fulfil the above mentioned need and to provide a thin adhesive film dressing having improved handling properties, which permits the dressing to be readily applied to the patient without touching, and thereby contaminating the adhesive surface of the film.

This object is achieved by providing a dressing which has a lateral (x) and a longitudinal (y) extension; the dressing comprising:
  a backing layer;
  a wound pad contoured by a pair of lateral edges extending in parallel to each other in the longitudinal direction, and a pair of longitudinal edges extending in parallel to each other in the lateral direction;
  an adhesive layer having a wound facing surface and a non-wound facing surface;
  the wound pad being arranged between the backing layer and the adhesive layer, wherein at least the backing layer extends beyond the periphery of the wound pad to define a border portion along the contour of the wound pad
  a release liner releasably attached to the wound facing surface of the adhesive layer;
  wherein the release liner is divided by a dividing line extending in the lateral direction (x) of the dressing to form at least a first removable portion, and a second removable portion; the first and second removable portions overlapping along the dividing line to form a first grip member; wherein the dividing line extends across the wound pad and is provided at a distance of less than 15 mm from at least one of the longitudinal edges of the wound pad.

A dressing according to the invention allows the user to apply the dressing very precisely at the end of an incision site. The dressing may be applied at the end of the incision site by positioning the edge portion of the wound pad to precisely cover the end of the incision.

As the dividing line, and consequently the grip member, is arranged at a distance of less than 15 mm from the longitudinal edge of the wound pad, the wound pad portion covered by the first removable portion of the release liner covers the entire incision. This allows for a large proportion of the absorbent area to be utilized for absorption of wound exudate. It also minimizes, or eliminates the risk of contaminating the wound since the second portion of the release liner, which covers only the portion of the wound pad separate from the incision, can be removed without touching or interfering with the incise.

The user can apply the dressing by slightly removing the first removable portion of the release liner, and positioning the dressing very precisely over the edge of the incise with the wound pad portion now partially uncovered from the first release liner portion. While slightly pressing the dressing onto the skin, the user can utilize both hands in removing the first removable portion and applying the dressing in a smooth and wrinkle free manner. As the second removable portion is located outside of the incise area, there is no risk that this piece of the release liner falls down onto the wound to cause contamination. After complete removal of the first removable portion of the release liner, and firm anchoring of this dressing part, the second removable portion of the release liner can be removed.

Preferably, the dividing line of the release liner is arranged at a distance of 3 to 10 mm from at least one of the longitudinal edges of the wound pad. This further enhances the utilization of the absorption area; i.e. wound pad, and allows the user to choose a smaller sized dressing having a wound pad which covers the whole incise.

In embodiments, the grip member comprises a first tab and a second tab. The first tab is formed from the longitudinal edge of the second removable portion being folded over itself, and the second tab is formed from the longitudinal edge of the first removable portion overlapping and extending beyond the folded longitudinal edge of the second removable portion.

Consequently, the first removable portion is removed by means of the first tab, and the second removable portion is removed by means of the underlying second tab.

This arrangement allows for the user to remove the portions of the release liners in the right order. It also eliminates the risk of contaminating the adhesive layer, since the overlap between the first and second tab prevents contaminants from entering the dressing layers. Furthermore, it is considered to be beneficial for packaging purposes as the dressings may be stored and packaged in a flat arrangement.

For many surgical procedures, e.g. hip or knee surgeries, caesarian sections, heart surgery and major abdominal surgeries, large, and relatively straight incisions may result. It is therefore desirable to use dressings of relatively large sizes. Typically these dressings are substantially rectangular in shape. In these situations, the application of the thin adhesive dressing becomes more complicated, as the larger sized dressings have an increased tendency to stick to themselves, and wrinkles are easily formed in the border portions of the dressings.

Therefore, in embodiments, the release liner of the dressing of the present invention may comprise a third removable portion; i.e. the release liner may be formed from three separate removable material portions. The above-mentioned dividing line may thus be a first dividing line and the above-mentioned grip member may be a first grip member. The release liner may be divided by a second dividing line extending in the lateral direction to form a third removable portion. The third removable portion overlaps with the first removable portion to form a second grip member.

In this arrangement, the first removable portion is removed completely, and the applicator can hold the dressing straight, in an essentially planar configuration by means of the portions of the dressings covered by the second and the third removable release liner portions.

The applicator may then position the dressing onto the incise by gently, and precisely anchoring the wound pad portion now uncovered by the first release liner portion onto the very end of the incision.

While anchoring the remaining part of the uncovered dressing portion onto the incision, the portion of the dressing covered by the second release liner portion may be ignored as there is no risk that this piece of the dressing falls down onto the wound, thereby causing contamination underneath. One hand can be used to firmly position the dressing to the skin along the length of the incision while holding the dressing covered by the third removable portion straight to eliminate the formation of wrinkles and also eliminating the risk of letting this portion of the dressing fall down onto the incise and interfere therewith. Thereafter, the third removable portion can be removed, and finally, the second removable portion of the dressing is removed. Thus, the dressing can be readily positioned on the patient in a stretched, completely sterile and wrinkle free condition.

The second grip member may comprise a first and a second tab. The first tab may be formed from the longitudinal edge of the third removable portion being folded over itself, and the second tab may be formed from the longitudinal edge of the first removable portion overlapping and extending beyond the folded longitudinal edge of the third removable portion.

Consequently, the third removable portion is removed by grasping the first tab of the second grip member. Also, the first removable portion can be removed by grasping the second tab of the second grip member, if the user should prefer to remove the first removable portion in this direction instead.

As mentioned above, this arrangement allows for the user to remove the portions of the release liner in the right order. It also provides a fully sterile dressing, and enables easy packaging of dressings.

Although embodiments having a three-piece release liner are advantageous, it should be understood that the inventive concept is also applicable to two-piece release liners. In such embodiments, instead of removing the first removable portion completely, before applying the dressing to the wound, the applicator would only partly separate the first removable portion from the adhesive layer and fold it over a non-removed part of the first removable portion. In this arrangement, the applicator can hold the dressing straight, in an essentially planar configuration by means of the portions of the dressings covered by the second removable portion and the folded first removable portion. The applicator may then position the dressing onto the incise by gently, and precisely anchoring the wound pad portion now partly uncovered by the first release liner portion onto the very end of the incision. While anchoring the remaining part of the uncovered dressing portion onto the incision, the portion of the dressing covered by the second release liner portion may be ignored as there is no risk that this piece of the dressing falls down onto the wound, thereby causing contamination underneath. One hand can be used to firmly position the dressing to the skin along the length of the incision while holding the dressing covered by the folded first removable portion straight to eliminate the formation of wrinkles and also eliminating the risk of letting this portion of the dressing fall down onto the incise and interfere therewith. Thereafter, the rest of the first removable portion can be removed, and finally, the second removable portion of the dressing is removed. Thus, the dressing can be readily positioned on the patient in a stretched, completely sterile and wrinkle free condition. In order to reduce the risk that the applicator removes the entire first removable portion at once before applying the dressing to the wound, the dressing may suitably comprise some type of applicator feedback means. Such applicator feedback means would have the function of informing the user that enough of the the first removable portion has been separated from the adhesive layer. Such feedback means may be implemented in various ways, for instance as tactile feedback or force feedback, and this is reflected in some example embodiments.

Thus, according to at least some embodiments, the release liner is a two-piece release liner which consists of said first removable portion and said second removable portion, wherein the dressing comprises means for locally providing a different retention force between said first removable portion and said adhesive layer, compared to the retention force between other areas of said removable portion and said adhesive layer, said means being spaced from said dividing line in the longitudinal direction (y).

The means for locally providing a different retention force, may for instance be a local modification of the adhesive layer. For instance, one or more discrete spots of the adhesive layer may be provided with more and/or stronger adhesive than other areas of the adhesive layer. Rather than discrete spotwise modification, the modification may be along a continuous line, for instance running in the lateral direction (x) of the dressing. Although it may be advantageous to locally increase the retention, as this inherently increases the resistance to continued peeling off the first removable portion, it should be understood that it is conceivable to instead locally lower the resistance, since a lowered resistance can also be a perceptible indication to the applicator.

Instead of or in addition to local modification of the adhesive layer, it is conceivable to modify the first removable portion, which is reflected in at least some embodiments.

Thus, in at least some embodiments, said first removable portion extends in the longitudinal direction (y) away from said grip member and said second removable portion to a longitudinal edge of the dressing, wherein said first removable portion is provided with a fold and/or score line extending in the lateral direction (x) across said first removable portion and being located between said dividing line and said longitudinal edge of the dressing. When the applicator starts to peel off the first removable portion he/she will perceive a certain retention force, and when the peeling has come to the fold and/or score line, he/she will perceive a different retention force between the adhesive layer and the first removable portion, thus reminding him/her of temporarily stop the removal of the first removable portion.

In embodiments, the adhesive layer comprises a centrally disposed apertured area and a non-apertured area extending beyond the apertured area in the lateral and longitudinal directions to form a non-apertured border portion which circumferents the perforated area.

By providing an apertured area being centrally disposed in the adhesive layer, the apertured area will cover the absorbent area of the dressing and will provide for a quick uptake of wound exudate into the wound pad. The non-apertured area covers the border portion of the wound pad and also the adhesive layer, and serves to provide a good adhesion to the skin.

For example, the apertured area may comprise a plurality of perforations extending through the wound contact layer.

The perforations allow for a quick absorption into the wound pad without compromising the tight fit to the skin provided by the adhesive layer, arranged to be in contact with the skin. Thereby, also the adhesive layer covering the wound pad will provide for a good adhesion to the skin.

In embodiments, the apertured area of the adhesive layer is arranged to cover at least 60% of the area of the wound pad.

The inventors have found that in order to achieve a good balance between adhesion, liquid absorption and liquid retention, it is beneficial to arrange the centrally disposed apertured area such that it covers the central, main portion of the wound pad, but leaving the edges of the wound pad free from apertures. The non-apertured border portions cover the edges of the wound pad, and forms a "liquid pocket" at these edges. Any liquid or body exudate absorbed by the wound pad will be prevented from leaking out to the border portion of the dressing due to the provision of the liquid pocket means at the edge portions of the wound pad. Leakage of liquid may substantially impair the adhesive properties, and may lead to poor adhesion of the dressing.

The apertured area may have a longitudinal extension corresponding to at least 60% of the longitudinal extension of the wound pad.

The liquid pocket function is especially important at the longitudinal edges of the wound pad. This is since the dressing, which is typically substantially rectangular in shape, is often arranged in longitudinal position, for example onto knee or hip surgery incisions. The longitudinal edge of the wound pad positioned downwards is therefore exposed to a large amount of body exudate flowing downwards when the user is standing up. The liquid pocket function is therefore considered to be important in this direction.

The dividing line forming said first and second removable portions may be provided in said non-apertured area of said adhesive layer. This is conceivable irrespective of the release liner being a two-piece or a three-piece release liner.

Thus, for a three-piece release liner, at least the first dividing line of the release liner is preferably arranged in the non-apertured area of the adhesive layer.

The grip member is consequently arranged in the non-apertured area of the adhesive layer. When the first portion of the release liner has been removed (or partly removed in case of a two-piece release liner), the dressing is applied in such a way that the apertures or perforations of the adhesive layer will be located to cover the incision, maximizing the absorption of wound exudate where it is needed; i.e. at the wound site. This arrangement also allows for a precise application of the dressing and ensures that the non-apertured area is not placed over the incision where absorption is needed.

For example, the dividing line (the first dividing line in case of a three-piece release liner) may be provided at the intersection between the apertured area and the non apertured area of the adhesive layer.

This arrangement secures optimal absorption over the wound.

In embodiments, at least one of the adhesive layer, the backing layer and the release liner is substantially transparent.

This is beneficial as it enables the applicator to distinguish the wound pad from the border portions such that the dressing can be positioned properly onto the incision.

In embodiments of the dressing having a three-piece release liner, at least part of the first grip member and/or the second grip member is coloured. In embodiments of the dressing having a two-piece release liner, said grip member is coloured.

When the release liner is either transparent or white, the coloured grip member(s) contrasts with the transparent or white colour. This contrast draws the attention to the grip members and directs the user towards removing the release liner in the correct way. The coloured grip members are also conceived as desirable for aesthetic reasons, both by the health care personnel and by the patients.

For example, in embodiments of the dressing having a three-piece release liner, at least part of the second tab of the first grip member and/or at least part of the second tab of the second grip member may be coloured. In embodiments of the dressing having a two-piece release liner, at least part of the second tab of the grip member is coloured.

In embodiments of the dressing having a three-piece release liner, the first grip member and/or the second grip member comprises at least one indicium. In embodiments of the dressing having a two-piece release liner, said grip member comprises at least one indicium.

The indicium functions to guide the applicator to remove the release liner portions in the correct manner.

For example, in embodiments of the dressing having a three-piece release liner the first tab of the first grip member and/or the first tab of the second grip member comprises at least one indicium. In embodiments of the dressing having a two-piece release liner, the first tab of the grip member comprises at least one indicium.

In embodiments of the dressing having a two-piece release liner, said first releasable portion may be coloured adjacent to said fold and/or score line. This guides the applicator in a similar way as the colouring of the second grip member described above with respect to a three-piece release liner.

In embodiments of the dressing having a two-piece release liner, said first releasable portion may comprise at least one indicium adjacent to said fold and/or score line. This guides the applicator in a similar way as the indicicum at the second grip member described above with respect to a three-piece release liner.

As explained previously, instead of or in addition to a fold and/or score line other means for locally providing a different retention force between said first removable portion and said adhesive layer. In such instance, at the area or adjacent to the area where said means is/are provided, the first removable portion may be coloured and/or comprise at least one indicium.

BRIEF DESCRIPTION OF THE DRAWINGS

The objectives and features of the invention will become more readily apparent from the following detailed description taken in conjunction with the accompanying drawings, in which.

DETAILED DESCRIPTION

In the following, some embodiments of the invention will be described in further detail with reference to the illustrative figures attached hereto.

Figure 1A:
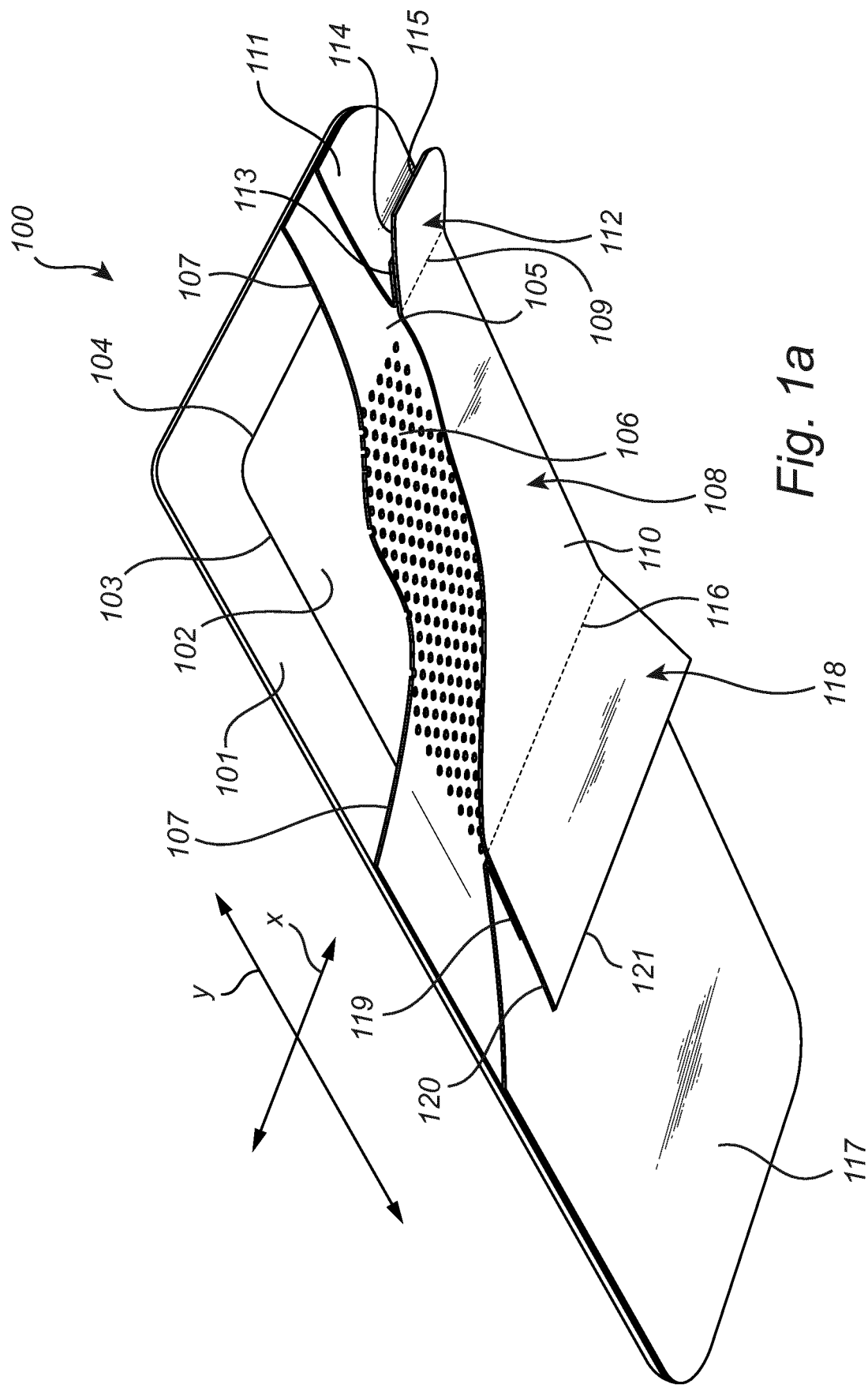
FIG. 1a illustrates a dressing according to at least one embodiment of the invention seen from the release liner surface; i.e. seen from the surface of the dressing intended to be in contact with the skin of a user.

FIG. 1a illustrates a dressing which has a lateral (x) and a longitudinal (y) extension.

As used herein, the term "lateral extension" or "lateral direction" is a direction running parallel to the minimum linear dimension of the article. The lateral direction is parallel to the x axis in the drawings.

A "lateral edge" of the dressing, wound pad, adhesive layer, apertured area or the release liner or any of its portions is an edge that extends in the longitudinal direction; i.e. parallel to the y axis.

The "longitudinal extension" or "longitudinal direction" is orthogonal to the lateral extension or direction. The longitudinal direction is consequently parallel to the y axis in the drawings.

A "longitudinal edge" of the dressing, wound pad, adhesive layer, apertured area or the release liner or any of its portions is an edge that extends in the lateral direction, i.e. parallel to the x axis.

FIG. 1a illustrates a dressing comprising a backing layer 101, a wound pad 102 contoured by a pair of lateral edges 103 extending in parallel to each other in the longitudinal direction, and a pair of longitudinal edges 104 extending in parallel to each other in the lateral direction, and an adhesive layer 105 having a wound facing surface 106 and a non-wound facing surface (not shown). The wound pad 102 is arranged between the backing layer 101 and the adhesive layer 105. The backing layer 101 extends beyond the periphery of the wound pad 102 to define a border portion 107 along the contour of the wound pad 102.

The adhesive layer 105 is arranged to receive body fluids, e.g. wound exudate from the wound while the wound pad 102 functions to absorb the wound exudate and transport it away from the wound by evaporating it from the top of the dressing; i.e. through the backing layer 101.

The backing layer 101 may be a thin film, sheet or membrane that is vapour permeable and waterproof. Examples of suitable materials for the backing layer 101 include, but are not limited to, polyurethane, polyethylene or polyamide films, silicone films, polyester based nonwoven materials, and laminates of polyester-based nonwoven materials and polyurethane films. A suitable material for use as a backing layer is polyurethane. For example, the backing layer 101 may be a polyurethane film having a thickness of from 5 to 40 µm, e.g. from 15 to 25 µm.

The backing layer 101 is typically bonded to the wound pad 102, for example, via an adhesive such as a pressure sensitive adhesive (e.g. an acrylic adhesive). The backing layer 101 may be bonded to the adhesive layer 105 in those parts of the backing layer 101 that extend beyond the wound pad.

The wound pad 102 may comprise an absorbent, conformable material such as for example, foams and/or cellulose based materials (e.g. hydrocellulose). The wound pad 102 may comprise a hydrophilic material, e.g. a hydrophilic foam. Suitable foam materials include, but are not limited to polyurethane foams.

The wound pad 102 may comprise one or several layers. For example, the wound pad 102 may comprise two or more layers having different properties laminated together. For example, the wound pad 102 can comprise a first absorbent layer on its wound-facing surface and a liquid distributing layer on its non-wound facing surface with the second absorbent layer being affixed to the backing layer 101.

The first absorbent layer may comprise a superabsorbent material, e.g. superabsorbent polymers (SAP) or superabsorbent fibers (SAF). For example, polyacrylic superabsorbent fibers may be suitable.

The liquid distributing layer may comprise a nonwoven material, e.g. viscose, polyester or blends thereof. The liquid distributing layer may be thinner than the first absorbent layer, and acts to spread the wound exudate upon entry from the adhesive layer 105.

The layers can be joined by adhesion, lamination, using pressure and heat.

The wound pad 102 may comprise additional layers, such as liquid transport layers, various combinations of foam and nonwoven layers laminated together.

The wound pad 102 may be embossed or pre-cut in order to enhance the flexibility of the dressing. Such cuts may spread the forces of movement, which allows the dressing to move with the body in a natural way. For example, the wound pad or any of its layers may comprise incisions as described in European Patent application No. 15164465.5, the entire contents of which are incorporated herein by reference.

The wound pad 102 may comprise one or more biologically active substance, e.g. a compound having an antimicrobial or wound healing effect. Examples of such compounds include, but are not limited to a silver compound such as silver salt and metallic silver, biguanide salts such as polyhexamethylene biguanide (PHMB) or any salts thereof, or polyhexamethyl guanide (PHMG) or any salts thereof, or chlorhexidine or any salts thereof, iodine, salicylic acid or any salt thereof, acetylsalicylic acid or any salt thereof, quarter ammonium salts such as benzethonium chloride, povidone-iodine (betadine), lactoferrin, xylitol, antimicrobial peptides such as human cationic antimicrobial protein 18 (hCAP18 or LL37), borneol, bismuth subgallate, antifungal pharmaceuticals, and antibiotics such as gentamycin, and streptomycin.

The adhesive layer 105 has a wound facing surface 106; i.e. a surface oriented towards the wound or skin of the wearer, and a non-wound facing surface (not shown), i.e. a surface oriented opposite to the adhesive surface when fitted to a wearer.

The adhesive layer may be an adhesive coating. The adhesive coating may cover at least part of the backing layer 101 and/or the wound pad 102. Alternatively, the adhesive layer may be a wound contact layer comprising an adhesive coating. The purpose of the adhesive layer is to adhere to the skin and keep the dressing in place during use. It is important that the adhesive used is skin-friendly and permits the removal of the dressing without causing damage to the skin. It should also have a strong adhesive effect to enable a prolonged time of use.

Examples of suitable adhesive coating materials include, but are not limited to, silicone gels, hot melt adhesives, acrylate adhesives, polyurethane gels, and hydrocolloid adhesives. In some embodiments, the adhesive is comprised of a material that is non-irritating to the skin, e.g. a silicone gel. Examples of suitable silicone gels include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4, In embodiments, the adhesive layer 105 is a wound contact layer comprising an adhesive coating. The wound contact layer may be comprised of any of a variety of materials known in the art and suitable for use in a dressing. For example, the wound contact layer may be comprised of a thin plastic film, or a laminate comprising a thin plastic film, coated with an adhesive. Suitable materials for the wound contact layer include, but are not limited to, polyolefin based films (such as polyethylene), polyamide, polyurethane, and silicone. A suitable material for use as wound contact layer is a thin polyurethane film. For example, the wound contact layer may be a polyurethane film having a thickness in the range of from 50 to 800 µm, e.g. from 100 to 400 µm, e.g. from 100 to 250 µm.

In such embodiments, the adhesive coating may constitute all of the wound contact surface 106 of the adhesive layer 105 or may cover only portions thereof.

The backing layer 101 extends beyond the periphery of the wound pad 102 to define a border portion 107 along the contour of the wound pad 102.

In embodiments, where the adhesive layer 105 is a wound contact layer comprising an adhesive coating, the adhesive layer 105 may be co-extensive with the backing layer 101, and have the same outer dimensions. Hence, both the backing layer 101 and the adhesive layer 105 define the border portion along the contour of the wound pad 102. The backing layer 101 and the adhesive layer 105 may be bonded to each other in those areas of both layers that extend beyond the periphery of the wound pad 102. Suitably, the border portions of the adhesive layer 105 comprises an adhesive coating.

In order to achieve sufficient adhesion properties, the border portion 107 has a width of 10 to 50 mm and extends along the contour of the wound pad. A smaller sized dressing may have a smaller border portion than a larger sized dressing. Preferably the border portion has a width of 20 to 30 mm and extends along the contour of the wound pad. This allows for easy handling and application of the product while still maintaining sufficient adhesion upon application.

A release liner 108 is releasably attached to the wound facing surface 106 of the adhesive layer 105.

As used herein, the term "releasably attached" means that the release layer may be peeled away from the rest of the wound dressing by hand. The removable portions of the release liner are releasably connected to each other meaning that they are connected such that the portions remain connected absent a separation force applied to one or all of the portions, and where the portions are capable of being separated upon the application of a separation force. The release liner 108 acts as a barrier that can protect the sterility of dressing including all of its layers before the dressing is used.

The release liner 108 may be made of any of a variety of suitable materials known in the art, e.g. polyethylene, polyester, polypropylene and silicone coated paper. For example, the release liner may be a polyethylene film having a thickness in the range of from 30 to 300 µm, e.g. from 50 to 150 µm.

The release liner 108 is divided by a first dividing line 109 extending in the lateral direction (x) of the dressing to form at least a first removable portion 110 and a second removable portion 111; the first and second removable portions 110 and 111 overlapping along the first dividing line 109 to form a first grip member 112. The dividing line 109 extends over the wound pad 102 and is provided at a distance of less than 15 mm from at least one of the longitudinal edges 104 of the wound pad 102. Thereby, the second removable portion 111 covers a portion of the wound pad 102.

The positioning of the first grip member 112 at a distance of less than 15 mm from the longitudinal edge 104 of the wound pad 102 allows for an improved positioning and application process of the dressing. The user may apply the dressing very precisely at the end of the incision site. One hand can be used to remove the first removable portion 110 in a stepwise manner and the other hand can assist by gently pressing the dressing onto the skin. The dividing line 109 of the release liner 108 sets the location of where to apply the dressing onto the incise. The user can focus on removing the first removable portion 110 in a completely sterile manner, and the second removable portion 111 of the release liner may be discharged during the anchoring procedure of the wound pad onto the skin. Since the portion of the dressing covered by the second removable portion 111 is located separate from the incision, there is no risk that this piece will fall down onto the wound causing contamination or contact with the incision. Also, the provision of the grip member 112 at a distance of less than 15 mm from the wound pad edge allows for the application to start at the end of the absorbent area; i.e. slightly beyond the end of the incision. This allows for a large proportion of the absorbent area to be utilized for absorption of wound exudate.

After complete removal of the first removable portion 110 of the release liner 108, and firm anchoring of this dressing part, the second removable portion 111 of the release liner 108 can be removed and attached to the skin of the patient.

It is considered beneficial, for sterility reasons, and for the purpose of protecting the surrounding skin from maceration, that the wound pad 102 overlaps the incision by at least 5 mm, e.g. about 10 mm. This will always be the case with a dressing of the invention since the first dividing line 109 of the release liner 108 is arranged such that the second removable portion 110 covers a portion of the wound pad 102.

The dressing of the invention is particularly suitable for exuding wounds, e.g. acute wounds, such as surgical wounds, cuts and abrasions.

In preferred embodiments, the first dividing line 109 of the release liner 108 is arranged at a distance of 3 to 10 mm from at least one of the longitudinal edges 104 of the wound pad 102.

This further enhances the utilization of the absorption area; i.e. wound pad 102, and allows the user to choose a smaller sized dressing having a wound pad which covers the whole incise.

In embodiments, the first grip member 112 comprises a first tab 113 and a second tab 114. The first tab 113 is formed from the longitudinal edge of the second removable portion 111 being folded over itself, and the second tab 114 is formed from the longitudinal edge 115 of the first removable portion 110 overlapping and extending beyond the folded longitudinal edge of the second removable portion 111.

The first tab 113 of the first grip member 112 may be folded over itself; i.e. away from the dividing line 109, suitably about 10 to 25 mm from the dividing line 109 of the release liner. The second tab 114 may suitably overlap and extend about 5 to 10 mm beyond the first tab 113. This is to prevent the clinician or the user from removing the portions of the release liner in the wrong order and to facilitate gripping and removal of the first removable portion 110.

Consequently, the first removable portion 110 is removed by means of the second tab 114, and the second removable portion 111 is removed by means of the underlying first tab 113.

This arrangement allows for the user to remove the portions of the release liner 108 in the correct order. It also eliminates the risk of contaminating the adhesive layer 105, since the overlap between the first and second tab prevents contaminants from entering the dressing layers. Furthermore, it is considered to be beneficial for packaging purposes as the dressings may be stored and packaged in a flat arrangement.

It is also conceivable, within the scope of the present invention, that the first tab 113 and the second tab 114 have the same length.

In alternative embodiments, both the first tab 113 and the second tab 114 are folded over themselves. Preferably, in such embodiments, the folded edges of the first and second tabs form an overlap of at least 5 mm. This is to protect the dressing from contamination before use.

Typically the dressing of the invention is substantially rectangular in shape. As used herein, the term "substantially rectangular" means that the longitudinal extension of the dressing is larger than the lateral extension. The corners of the wound pad or the dressing may be rounded or sharp.

In many surgical procedures, relatively large dressings, having a substantially rectangular shape are usually used. Examples of such surgical procedures include, but are not limited to hip or knee surgeries, caesarian sections, heart surgeries and major abdominal surgeries. In these procedures, large incisions producing a vast amount of wound exudate result. As the size of the dressing must be increased, the complexity of the application procedure and the risk of causing contamination at the wound site also increases. The larger sized dressings have an increased tendency to stick to themselves, and wrinkles are easily formed in the border portions of the dressings.

Therefore, as further illustrated in FIG. 1, the release liner 108 may be divided by a second dividing line 116 extending in the lateral direction to form a third removable portion 117. The third removable portion 117 overlaps with the first removable portion 110 to form a second grip member 118.

The release liner 108 of the dressing of the present invention thus comprises three separate, releasably connected removable portions.

The second grip member 118 may be positioned at least 80 mm from the first grip member 112 in order to have a sufficient adhesive area which will be used to anchor the dressing to the wound and the skin.

The length of the dressing in the longitudinal direction may be in the range of from 10 to 50 cm, for example in the range of from 12 to 40 cm, and preferably in the range of from 15 to 35 cm. The width of the dressing in the lateral direction may be from 5 to 25 cm, e.g. from 7 to 20 cm, and preferably in the range of from 9 to 15 cm. The length of the wound pad in the longitudinal direction is typically in the range of from 7 to 40 cm, and preferably in the range of from 9 to 30 cm. The width of the wound pad in the lateral direction may be from 2 to 18 cm, e.g. from 4 to 10 cm. These dimensions are suitable for surgical wounds with various lengths of incisions.

In embodiments of the invention, the second grip member 118 may comprise a first 119 and a second tab 120. The first tab 119 may be formed from the longitudinal edge of the third removable portion 117 being folded over itself, and the second tab 120 may be formed from the longitudinal edge 121 of the first removable portion 110 overlapping and extending beyond the folded edge of the third removable portion 117.

The first tab 119 may be folded back about 10 to 25 mm from the second dividing line 116 of the release liner. The second tab 120 may overlap and extend about 5 to 10 mm beyond the first tab. This is to prevent the clinical or the user from removing the portions of the release liner in the wrong order.

Consequently, the third removable portion 117 is removed by grasping the first tab 119 of the second grip member 118.

As mentioned above, this arrangement allows for the user to remove the portions of the release liner in the right order. It also provides a fully sterile dressing, and enables packaging of the dressings in a flat arrangement.

The dressing of the invention may be prepared by any well known manufacturing technique. First, all the layers of the dressing are assembled by means of adhesion, lamination or any technique known in the art. Thereafter, the release liner is applied to the dressing. The removable portions of the release liner may be provided as three separate webs which are assembled together before application onto the dressings. The second and the third removable portions may be either pre-folded before application, or they may be provided as flat webs which are folded during manufacturing.

The dressing of the invention is not restricted for use on incisions following surgery, but may be used for all types of wounds. It may also form part of a negative pressure wound treatment system. In such embodiments, the dressing comprises a port in the backing layer that extends into the wound pad and allows fluid communication between the wound pad and a conduit connected to the port.

Figure 1B:
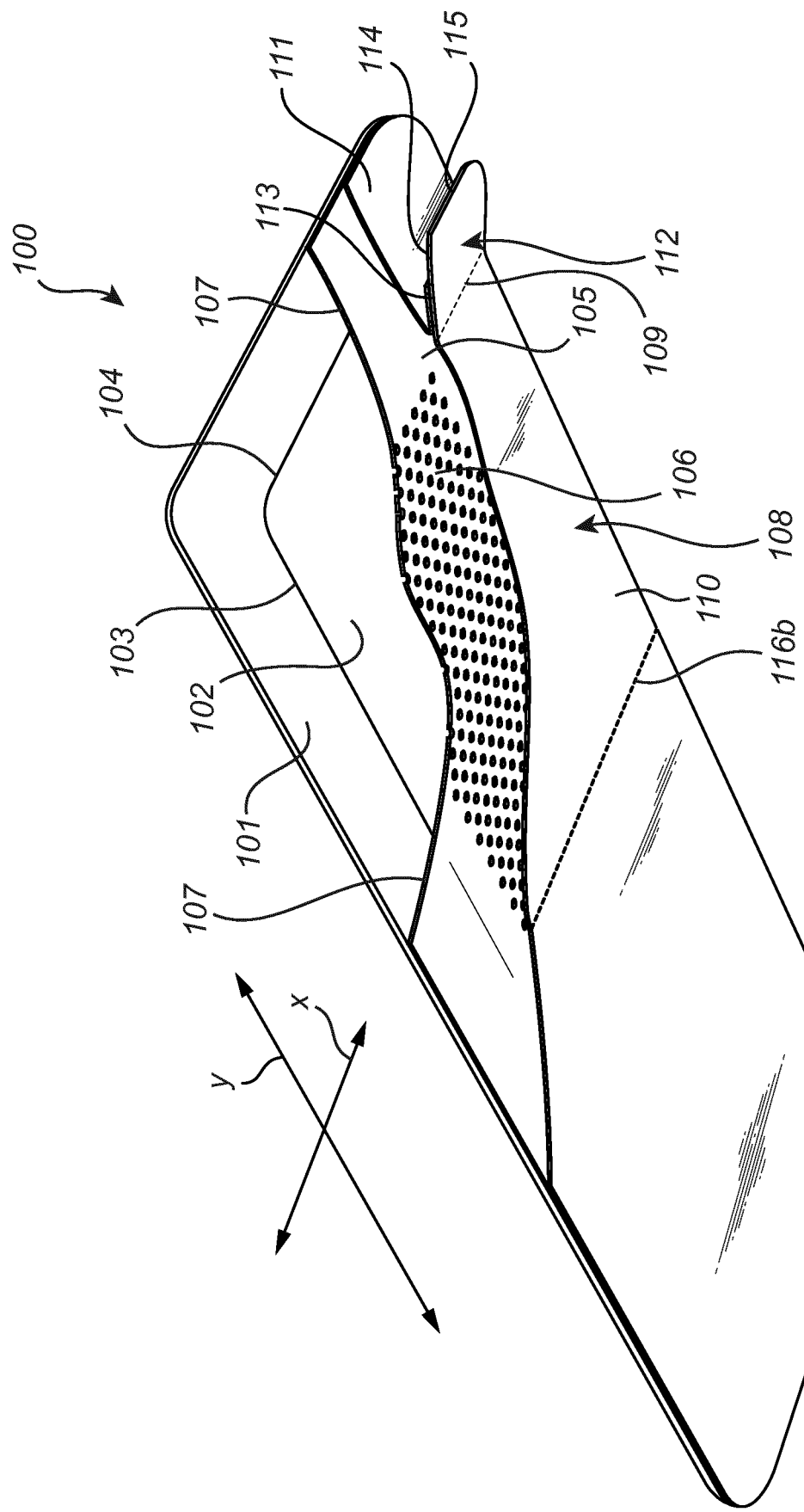
FIG. 1b illustrates a dressing according to at least another embodiment of the invention seen from the release liner surface; i.e. seen from the surface of the dressing intended to be in contact with the skin of a user.

In FIG. 1b an embodiment of the invention is illustrated which is similar to the embodiment illustrated in FIG. 1a. However, the dressing in FIG. 1b lacks a third removable portion, and a second grip member. Instead the first removable portion 110 extends from the dividing line 109 and the second removable portion 111 all the way to a longitudinal edge of the dressing. The first removable portion 110 is provided with a score line 116b, which functions as a means for locally changing the retention between the first removable portion and the adhesive layer 105.

Similar to the embodiment in FIG. 1a, in the embodiment of FIG. 1b the first grip member 112 is positioned at a distance of less than 15 mm from the longitudinal edge 104 of the wound pad 102 in order to allow for an improved positioning and application process of the dressing. The user may suitably start by peeling away a part of the first removable portion 110, and when the peeling reaches the score line 116b, the user will perceive a change in retention force, which serves as an indication that the peeling may temporarily be stopped. Next, the user may apply the dressing very precisely at the end of the incision site. One hand can be used to remove the first removable portion 110 in a stepwise manner and the other hand can assist by gently pressing the dressing onto the skin. The dividing line 109 of the release liner 108 sets the location of where to apply the dressing onto the incise. The user can focus on continuing removing the first removable portion 110 in a completely sterile manner, and the second removable portion 111 of the release liner may be discharged during the anchoring procedure of the wound pad onto the skin. Since the portion of the dressing covered by the second removable portion 111 is located separate from the incision, there is no risk that this piece will fall down onto the wound causing contamination or contact with the incision. Also, the provision of the grip member 112 at a distance of less than 15 mm from the wound pad edge allows for the application to start at the end of the absorbent area; i.e. slightly beyond the end of the incision. This allows for a large proportion of the absorbent area to be utilized for absorption of wound exudate. During manufacture, before applying the release liner to the rest of the dressing, a fold line may be created on the release liner portion by rotating a knife having a slightly blunt edge that is pressed against the release liner, and suitably an anvil roller is present on the opposite side of the release liner. For making a score line, a circular cutting edge may be blunt and sharp alternatingly along circumference, so as to provide scores/perforations in the first removable portion.

Figure 2A:
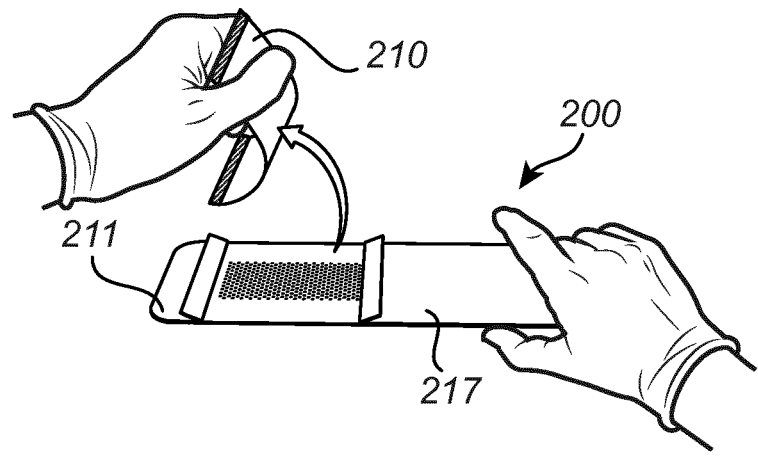
FIGS. 2a-c illustrate the application of a dressing according to at least one embodiment of the invention onto the knee of a patient.
Figure 2B:
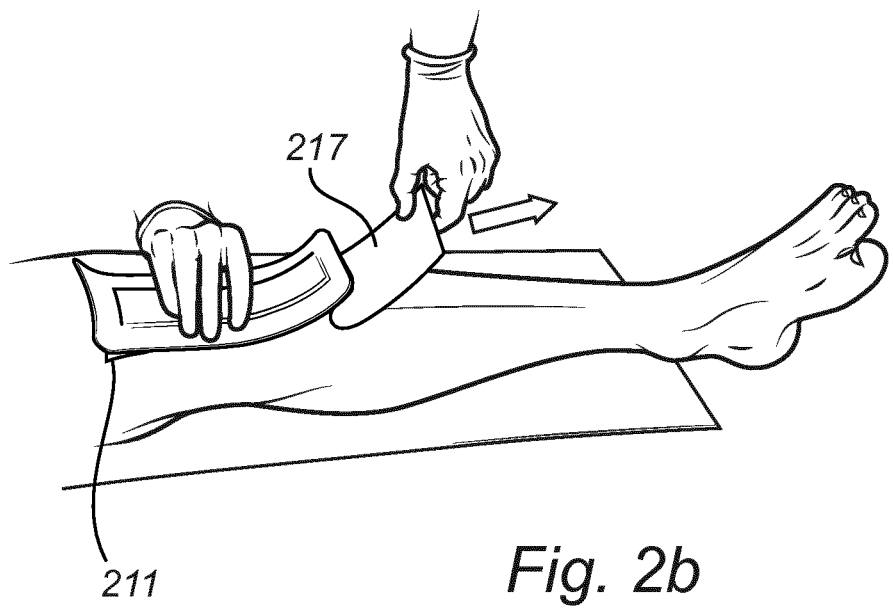
Figure 2C:
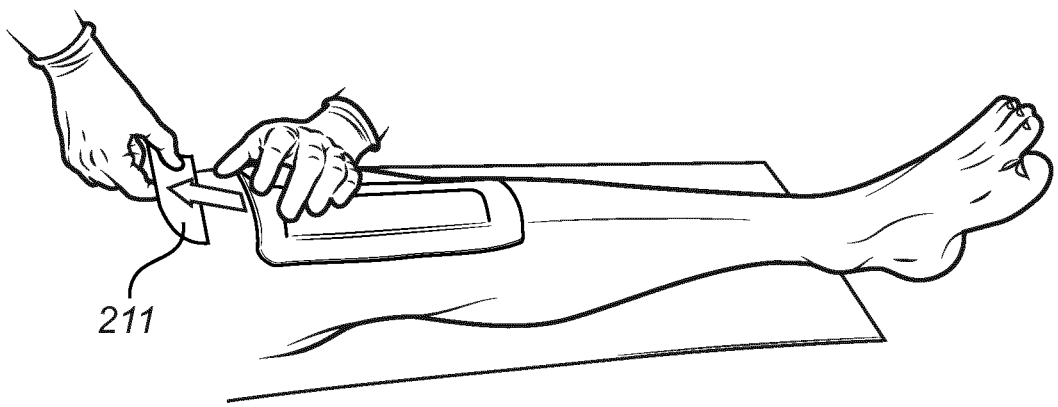

In FIGS. 2a-c, the application procedure of a dressing comprising a release liner with three removable portions onto the knee of a patient is illustrated.

As a first step, the first removable portion 210 is removed completely, and the applicator can hold the dressing straight, in an essentially planar configuration by means of the portions of the dressings covered by the second 211 and the third 217 removable release liner portions (see FIG. 2a).

As illustrated in FIG. 2b, the applicator may then position the dressing 200 onto the incise by gently, and precisely anchoring the wound pad portion now uncovered by the first release liner portion onto the very end of the incision.

While anchoring the dressing portion uncovered from the first removable portion 210 onto the incision, the part of the dressing covered by the second release liner 211 portion may be ignored as there is no risk that this piece of the dressing falls down onto the wound, thereby causing contamination underneath. One hand can be used to firmly position the dressing to the skin along the length of the incision while holding the dressing covered by the third removable portion 217 straight to eliminate the formation of wrinkles and also eliminating the risk of letting this portion of the dressing fall down onto the incise. Thereafter, the third removable portion 217 can be removed while simultaneously pressing the dressing against the skin.

In the last stage, the second removable portion 211 of the dressing is removed and anchored to the skin (FIG. 2c). Accordingly, the dressing according to this embodiment allows for an improved control of large and thin dressings and facilitates the application thereof. The procedure hinders the border corners of the dressing to fold, and the dressing can be readily positioned on the patient in a stretched, completely sterile and wrinkle free condition.

Figure 3A:
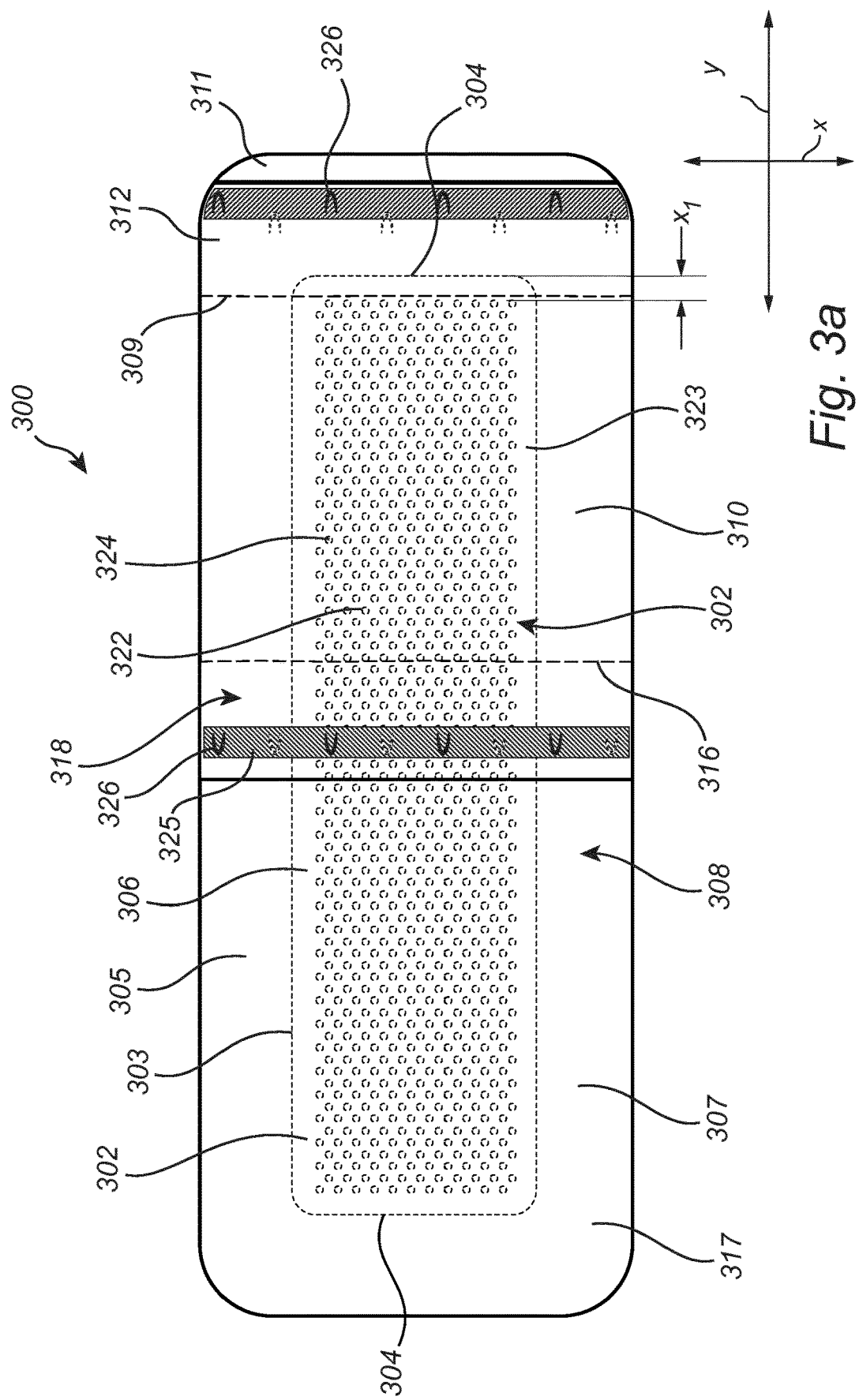
FIG. 3a illustrates a dressing according to one embodiment of the invention, seen from the release liner surface; i.e. the dressing surface to be in contact with the skin of a user.

FIGS. 3a and b illustrate an exemplary embodiment of the dressing according to the invention.

The dressing 300 comprises a backing layer (not shown), a wound pad 302 contoured by a pair of lateral edges 303 extending in parallel to each other in the longitudinal direction, an adhesive layer 305 having a wound facing surface 306 and a non-wound facing surface (not shown). The wound pad 302 is arranged between the backing layer and the adhesive layer 305, wherein at least the backing layer extends beyond the periphery of the wound pad 302 to define a border portion 307 along the contour of the wound pad 302. A release liner 308 is releasably attached to the wound facing surface 306 of the adhesive layer 305. The release liner 308 is divided by a first dividing line 309 to form a first removable portion 310 and a second removable portion 311. The first and the second removable portions 310 and 311 overlap along the dividing line 309 to form a first grip member 312. The dividing line 309 extends over the wound pad 102 and is provided at a distance, x1, of less than 15 mm from at least one of the longitudinal edges 304 of the wound pad 302.

The adhesive layer 305 comprises a centrally disposed apertured area 322 and a non-apertured area 323 extending beyond the apertured area 322 in the lateral and longitudinal directions to form a non-apertured border portion which circumferents the apertured area 322.

As used herein, the term "apertured area" means an area of the adhesive layer comprising at least one aperture, preferably a plurality of apertures or perforations extending through the adhesive layer allowing fluid to pass therethrough. The apertures or perforations may be of various shapes and sizes. The apertured area may for instance comprise one large aperture which constitutes the entire apertured area. Alternatively, the apertured area comprises a plurality of apertures or perforations. The perforations or apertures may have different shapes and densities along varying regions of the adhesive layer 305, and may be arranged in a regular or irregular pattern.

During the healing process, wounds produce exudate. This exudate may enter the wound pad 302 through the apertured area 322 of the adhesive layer 305. The apertured area 322 allows for a quick uptake of wound exudate into the wound pad 302, thereby keeping the wound clean and promoting a faster healing. The exudate is absorbed into the wound pad 302, and is transported away by evaporation from the backing layer.

This construction allows for effectively directing the exudate absorption to the wound pad 302, and trapping the exudate therein. An improved absorption of liquid centrally is thereby obtained; i.e. where the wound incision is located. In order to improve the adhesion to the skin, the border portion 323 of the wound pad and of the dressing 307 is non-apertured. This is advantageous in terms of the product's ability to stay on the skin since apertures may impair the adhesion properties of the adhesive layer 305. Furthermore, the border portion 307 is prevented from wetting by wound exudate, which may cause the adhesive border to become moist and loose adhesive power. The adhesive border portions 323 and 307 provide a tight fit of the dressing to the skin.

Preferably, the apertured area 322 comprises a plurality of perforations 324.

The perforations 324 allow for a quick uptake of wound exudate into the wound pad 302, without compromising the tight fit to the skin provided by the adhesive layer 305.

Typically, the plurality of perforations 324 are arranged in a predetermined, regular pattern. The perforations may have a diameter of from 0.5 mm to 10 mm, e.g. from 1 to 5 mm, e.g. from 1 to 2 mm.

In embodiments, the apertured area 322 of the adhesive layer 305 is arranged to cover at least 60% of the area of the wound pad 302.

As mentioned above, accumulation of wound exudate can wet the adhesive border portions, which may contribute to detachment of the dressing. By arranging the adhesive layer 305 such that the apertured area 322 covers the central part of the wound pad 302, i.e. at least 60% of the area of the wound pad, a liquid pocket effect is achieved at the intersection between the apertured 322 and non-apertured 323 areas. Liquid or body exudate absorbed into the wound pad 302 is prevented from leaking out to the border portion of the adhesive layer 305 (or dressing), and the adhesiveness of the border portion thus remain substantially unaffected. A good balance between a tight fit to the skin, liquid absorption and liquid retention is thus achieved.

The apertured area 322 may have a longitudinal extension corresponding to at least 60% of the longitudinal extension of the wound pad 302.

The liquid pocket function is especially important in the longitudinal direction; i.e. at the longitudinal edges 304 of the wound pad 302. This is since the dressing, being typically substantially rectangular in shape, is often arranged in vertical position, such as for example to cover an incision resulting from a knee or hip surgery. One of the longitudinal, shorter edges of the wound pad 302 is thus arranged to receive a large amount of body exudate flowing downwards when the user is standing up.

The extension of the apertured area 322 in the longitudinal direction may thus be larger than in the lateral direction.

This way, the liquid pocket effect is enhanced at the longitudinal edges 304. Also, if the dressing is to be applied on less straight incisions, the lateral extension of the apertured area 322 is desirably as large as possible to fully utilize the absorbent potential of the wound pad.

In embodiments, the apertured area 322 has a longitudinal extension corresponding to at least 70%, e.g. at least 80% of the longitudinal extension of the wound pad.

For example, the non-apertured area 323 may be arranged to extend over the wound pad 302 about 10-40 mm from the longitudinal edges 304 of the wound pad 302, and 0 to 15 mm, e.g. 2.5 to 7.5 mm from the lateral edges 303 of the wound pad 302.

The first dividing line 309 may be provided in the non-apertured area 323 of the adhesive layer 305.

Consequently, the first grip member 312 is arranged in the non-apertured area 323 of the adhesive layer 305.

This is beneficial as the apertured area 322 should be arranged to cover the total length of the incision to enable optimal absorption of wound exudate. It also further improves the positioning and the precise application of the dressing, and ensures that the non-apertured area 323 is not placed over the incision where absorption is needed.

For example, the first dividing line may be provided at the intersection between the apertured area 322 and the non-apertured area 323 of the adhesive layer 305.

As illustrated in FIG. 3a, the first dividing line 309 is provided at the intersection between the apertured area 322 and the non-apertured area 323. Alternatively, it may arranged at a distance of about 5 mm from the longitudinal edge of the apertured area 322, for example 2 to 3 mm from the longitudinal edge of the apertured area 322.

In embodiments, at least one of the adhesive layer 305, the backing layer and the release liner 308 is substantially transparent.

This is beneficial as it enables the applicator to distinguish the wound pad 302 from the border portions 307 such that the dressing can be positioned properly onto the incision.

Preferably, the backing layer and the adhesive layer are both transparent.

The release liner may have any colour, but is preferably white or transparent.

For example, at least part of the first grip member 312 and/or the second grip member 318 is coloured.

The coloured portion of the grip member(s) 312 and 318 is denoted 325 in FIG. 3a.

The colour may be any colour that contrasts with the colour of the release liner 308, e.g. green, blue, purple, red, black etc. The use of a colour on part of the grip member(s) 312 and/or 318 creates a contrast with the release liner 308, which, for example, is white or substantially transparent. The contrast is provided to draw attention to the first removable portion 310, which is to be removed first. Thus, it allows the applicator to remove the portions of the release liner 308 in the correct order.

It is also conceived as desirable for aesthetic reasons, both by the health care personnel and by the patients.

For example, at least part of the second tab of the first grip member 312 and/or the second tab of the second grip member 318 is coloured.

In embodiments, the first grip member 312 and/or the second grip member 318 comprises at least one indicium 326.

For example, the first tab of the first grip member 312 and/or the first tab of the second grip member 318 comprises at least one indicium.

Figure 3B:
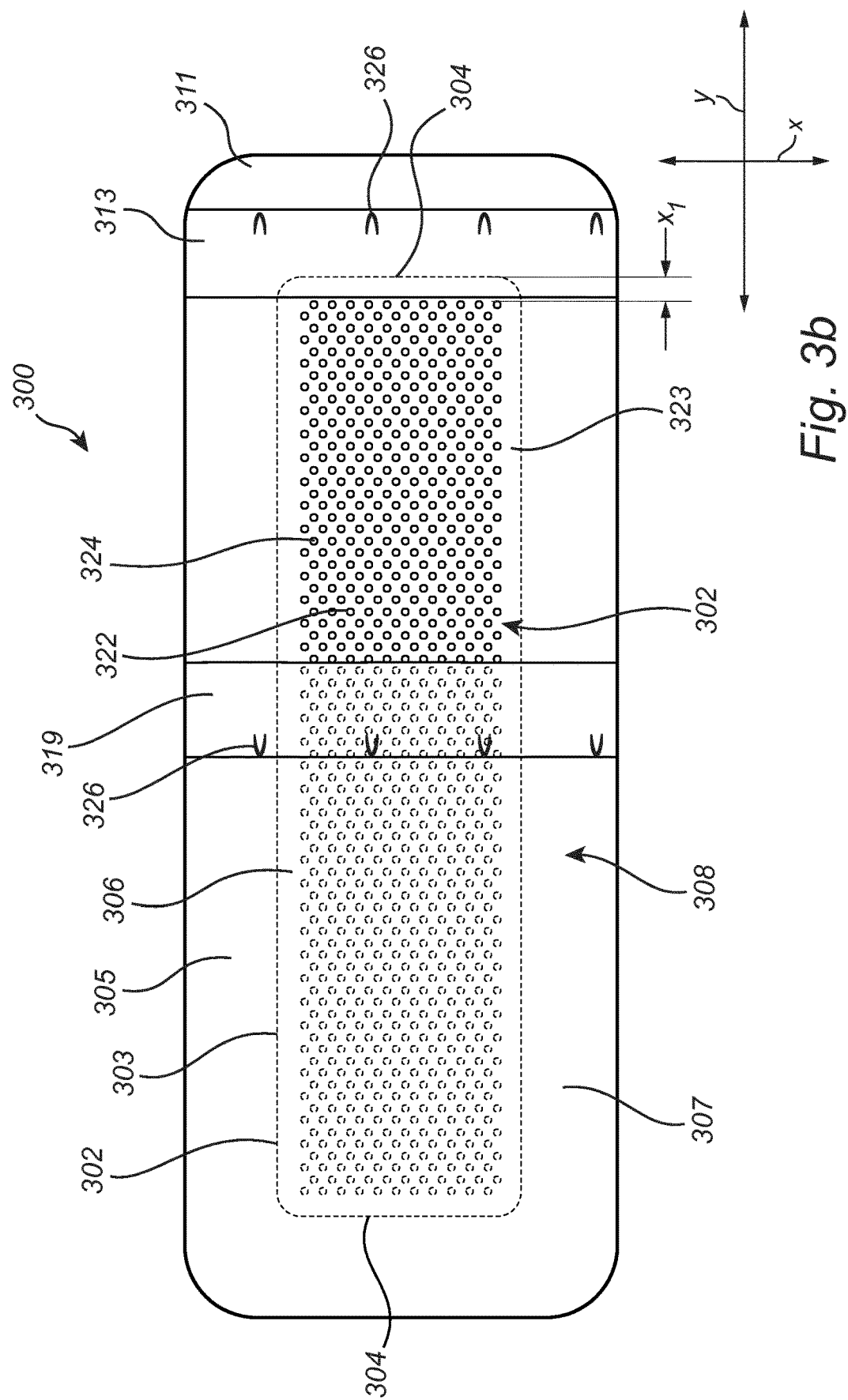
FIG. 3b illustrates the dressing in FIG. 3a, where the first removable portion of the release liner has been removed.

The indicium 326 may be any type of indicium which may be used to denote removal of the different portions of the release liner 308. The indicium 326 may e.g. be an arrow as illustrated in FIGS. 3a and 3b. This is to further indicate the order in which the release liner portions should be removed.

Alternatively, the indicium may be a number to even further clarify the order by which the release liner should be removed. For example, the first tab of the first grip member 312 may be indicated with 1 to symbolize that the first removable portion 310 should be removed first. The second tab of the second grip member 318 (if present) may be indicated with 2 to illustrate that the third removable portion 317 should be removed thereafter. In addition, the second tab of the first grip member 312 may be indicated with 3 to illustrate that the second removable portion 311 should be removed last.

It is also conceivable that such indicium, e.g. numbers, may be provided anywhere on the surface of the release liner portions. For example, the first removable portion 310 may be indicated with 1, the third removable portion 317 may be indicated with 2, and the second removable portion 311 may be indicated with 3.

As illustrated in FIGS. 3a and 3b, in one preferred embodiment, at least a part 325 of the second tab of the first grip member 312 is coloured, whereas the first tab of the first grip member 312 comprises an indicium 326. In embodiments where a three piece release liner is used, at least a part 325 of the second tab of the second grip member 318 is coloured, and the first tab of the second grip member 318 comprises an indicium 326. As can be seen in FIG. 3a, the colour of the first and second grip members 312 and 318 draws the attention of the user to the portion of the release liner which is to be removed first (i.e. the first removable portion 310). As illustrated in FIG. 3b, once the first removable portion 310 of the release liner 308 has been removed, the indicium 326 of the grip members 312 and 318 become visible to further illustrate how to remove the release liner portions.

Other embodiments of the invention will be apparent to those skilled in the art from consideration of the specification or practice of the invention disclosed herein. It is intended that the specification and examples be considered as exemplary only, with the true scope of the invention being indicated by the following claims.

The invention claimed is:

1. A dressing having a lateral (x) and a longitudinal (y) extension; said dressing comprising:
   a backing layer;
   a wound pad having a size contoured by a pair of lateral edges extending in parallel to each other in the longitudinal direction, and a pair of longitudinal edges extending in parallel to each other in the lateral direction, wherein the wound pad has a length from 7 cm to 40 cm in the longitudinal direction;
   an adhesive layer having a wound facing surface and a non-wound facing surface;
   said wound pad being arranged between said backing layer and said adhesive layer, wherein at least said backing layer extends beyond the periphery of said wound pad to define a border portion along the contour of said wound pad, wherein said adhesive layer covers said size of said wound pad and extends beyond the periphery of said wound pad in said lateral direction (x) and said longitudinal direction (y);
   a three-piece release liner having a first removable portion, a second removable portion, and a third removable potion releasably attached to said wound facing surface of said adhesive layer;
   wherein said three-piece release liner is divided by a first dividing line extending in the lateral direction (x) of the dressing to form at least said first removable portion, and said second removable portion; said first and second removable portions overlapping along said dividing line to form a first grip member; wherein said first dividing line extends across said wound pad and is provided at a distance of less than 15 mm from at least one of said longitudinal edges of said wound pad,
   wherein said three-piece release liner is divided by a second dividing line extending in said lateral direction (x) to form said third removable portion; said third removable portion overlapping with said first removable portion along said second dividing line to form a second grip member, wherein said second dividing line extends across said wound pad,
   wherein said first grip member comprises a first tab and a second tab, wherein said first tab is formed from said longitudinal edge of said second removable portion being folded over itself, and the second tab is formed from said longitudinal edge of said first removable portion overlapping and extending beyond said folded longitudinal edge of said second removable portion, wherein said second tab of said first grip member extends beyond said first tab of said first grip member; and
   wherein said second grip member comprises a first tab and a second tab, wherein said first tab is formed from said longitudinal edge of said third removable portion being folded over itself, and said second tab is formed from said longitudinal edge of said first removable portion overlapping and extending beyond said folded edge of said third removable portion, wherein said second tab of said second grip member extends beyond said first tab of said second grip member.

2. The dressing according to claim 1, wherein said first removable portion extends in the longitudinal direction (y) away from said grip member and said second removable portion to a longitudinal edge of the dressing, wherein said first removable portion is provided with a fold and/or score line extending in the lateral direction (x) across said first removable portion and being located between said dividing line and said longitudinal edge of the dressing.

3. The dressing according to claim 2, wherein said first removable portion is coloured, or wherein said first removable portion comprises at least one indicium adjacent to said fold and/or score line.

4. The dressing according to claim 1, wherein said adhesive layer comprises a centrally disposed apertured area, and a non-apertured area extending beyond said apertured area in the lateral and longitudinal directions to form a non-apertured border portion which circumferents said apertured area.

5. The dressing according to claim 4, wherein said apertured area comprises a plurality of perforations extending through said adhesive layer.

6. The dressing according to claim 4, wherein said apertured area of said adhesive layer is arranged to cover at least 60% of the area of said wound pad.

7. The dressing according to claim 4, wherein said apertured area has a longitudinal extension corresponding to at least 60% of the longitudinal extension of said wound pad.

8. The dressing according to claim 4, wherein said dividing line forming said first and second removable portions is provided in said non-apertured area of said adhesive layer.

9. The dressing according to claim 4, wherein said dividing line forming said first and second removable portions is provided at the intersection between said apertured area and said non-apertured area of said adhesive layer.

10. The dressing according to claim 1, wherein said second tab of said first grip member extends at least 5 mm beyond said first tab of said first grip member.

11. The dressing according to claim 10, wherein said second tab of said second grip member extends at least 5 mm beyond said first tab of said second grip member.

12. The dressing according to claim 1, wherein said second tab of said first grip member extends beyond said at least one of said longitudinal edges of said wound pad in said longitudinal direction (y).

13. The dressing according to claim 12, wherein said second tab of said second grip member does not extend beyond a longitudinal edge of said wound pad in said longitudinal direction (y).

14. The dressing according to claim 1, wherein said dividing line of said release liner is provided at a distance of from 3 to 10 mm from at least one of said longitudinal edges of said wound pad.

15. The dressing according to claim 1, wherein at least one of said adhesive layer, said backing layer and said release liner is substantially transparent.

16. The dressing according to claim 1, wherein at least part of said first grip member and/or said second grip member is coloured.

17. The dressing according to claim 1, wherein at least part of said second tab of said first grip member and/or said second tab of said second grip member is coloured.

18. The dressing according to claim 1, wherein said first grip member and/or the second grip member comprises at least one indicium.

19. The dressing according to claim 1, wherein said first tab of said first grip member and/or said first tab of said second grip member comprises at least one indicium.

20. The dressing according to claim 1, wherein said third removable portion has a dimension along said longitudinal direction (y) that is greater than a dimension of said second removable portion along said longitudinal direction (y).

* * * * *